(12) United States Patent
Vaisburd et al.

(10) Patent No.: US 7,020,315 B2
(45) Date of Patent: Mar. 28, 2006

(54) SAG CORRECTION

(75) Inventors: Alexander Vaisburd, Haifa (IL); Leonid Yakubovsky, Kiryat-Bialik (IL); Raed Khamaisi, Kfar-Kana (IL)

(73) Assignee: Elgems Ltd., Tirat-Hacarmel (IL)

(*) Notice: Subject to any disclaimer, the term of this patent is extended or adjusted under 35 U.S.C. 154(b) by 773 days.

(21) Appl. No.: 09/757,990

(22) Filed: Jan. 10, 2001

(65) Prior Publication Data
US 2002/0122575 A1 Sep. 5, 2002

(51) Int. Cl.
*G06K 9/00* (2006.01)

(52) U.S. Cl. .................. 382/131; 378/4; 378/901; 600/425

(58) Field of Classification Search .......... 382/128, 382/129, 130, 131, 132, 133, 134; 378/65, 378/206, 164, 62, 4, 21, 23, 24, 25–27, 901; 600/410, 420, 483, 301, 213, 407, 425, 524; 250/363.04; 424/6.4, 9.4
See application file for complete search history.

(56) References Cited

U.S. PATENT DOCUMENTS

| | | | | |
|---|---|---|---|---|
| 4,357,535 A | * | 11/1982 | Haas | 378/57 |
| 4,894,855 A | * | 1/1990 | Kresse | 378/196 |
| 5,583,903 A | * | 12/1996 | Saito et al. | 378/19 |
| 5,872,829 A | * | 2/1999 | Wischmann et al. | 378/164 |
| 5,995,581 A | * | 11/1999 | Ozaki | 378/20 |
| 6,011,828 A | * | 1/2000 | Hardy et al. | 378/65 |
| 6,128,522 A | * | 10/2000 | Acker et al. | 600/411 |
| 6,341,152 B1 | * | 1/2002 | Sugihara | 378/4 |
| 6,505,064 B1 | * | 1/2003 | Liu et al. | 600/420 |
| 2002/0081008 A1 | * | 6/2002 | Wollenweber | 382/131 |

* cited by examiner

Primary Examiner—Kanjibhai Patel
Assistant Examiner—Abolfazl Tabatabai
(74) Attorney, Agent, or Firm—Fenster & Co

(57) ABSTRACT

A method for the determination of the effects of variable sag of a supporting element of a support system on an image of a slice of a subject, comprising acquiring an image of a slice subject at an imaging position, determining said sag of said support element at said imaging position, and optionally correcting the image to compensate for the sag.

34 Claims, 6 Drawing Sheets

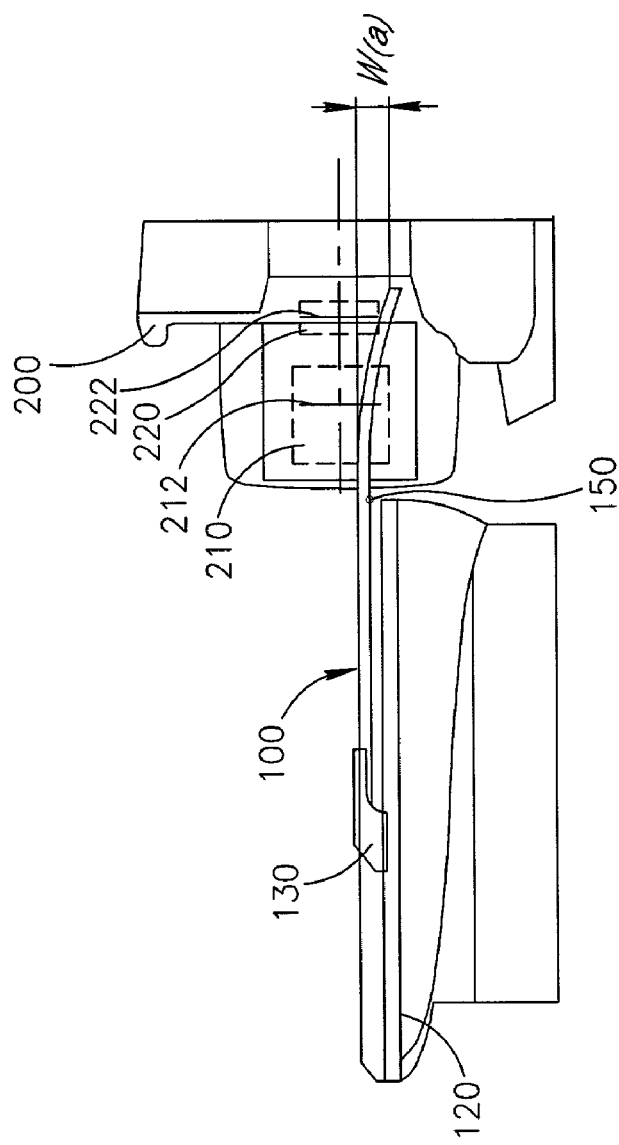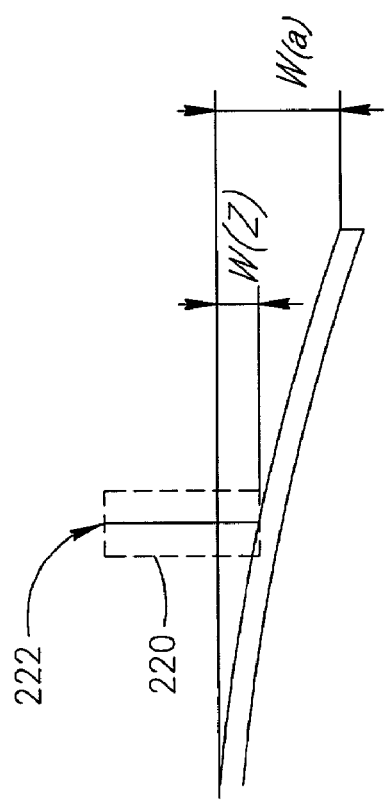

SAG CORRECTION

FIELD OF THE INVENTION

The present invention relates to multi-modality imaging systems.

BACKGROUND OF THE INVENTION

For many purposes it is of value to use more than one imaging method to construct images of a subject, and to compare the different images. Until recently an image would be taken one system—for example using X-rays, and at another time, and perhaps at another location, another image would be acquired, for example by a radioisotope imaging system using gamma rays.

A problem with using more than one image is the issue of alignment. If two images are not aligned properly, then the comparison of findings from one image with those of another image will be faulty. Thus true correlations between some details will be missed and false correlations and/or other artifacts are likely to be encountered.

Recently multi-modality imaging systems have become available, in which more than one imaging system use a common patient-support system. In many such machines the imaging equipment of the different systems is held by one or more gantries. The subject is supported and moved from one imaging area to another imaging area by a support system, often comprising a supporting element upon which the subject lies, for example a stretcher, and a base, or table, which holds, supports and controls the motion of the supporting element.

In medical imaging, the part of the patient's body (in some situations: the whole patient) to be scanned (herebelow: the subject) is generally substantially the same for all the imaging systems. The stretcher, on which the patient lies, is differentially extended from the table into the gantry volume, to position the subject in the different imaging planes. The stretcher, which is generally cantilever supported, sags differently at each imaging plane, because it is differentially extended. As a result of the differential sag, the images from the various imaging systems are not properly aligned. While this is not a problem for simple image viewing, it may be a problem for systems in which the images interact, as for example where a CT (X-ray computerized tomography) image is used for attenuation correction for a NM (Nuclear Medicine) gamma ray image. Such corrections are well known in the art.

SUMMARY OF THE INVENTION

An aspect of some embodiments of the invention is concerned with the determination of the sag of a stretcher in the imaging volume of each of the modalities, thus enabling accurate alignment of the images obtained in the various modalities.

An aspect of some embodiments of the invention provides a method and an apparatus which facilitates the measurement of the sag of a stretcher on which a patient is supported.

In some embodiments of the invention an object, or part of an object, which is part of the patient support system is imaged together with the patient to facilitate the measurement of the sag of the stretcher.

An aspect some embodiments of the present invention is a method of determining the sag of the stretcher at points where the sag is not measured. In some embodiments of the invention the sag is determined at one position, for example using one modality, and is computed at another position, for example in the imaging volume of the other modality.

An aspect of some embodiments of the present invention is the alignment of the images constructed by the various imaging systems in the multi-modality imaging system by taking into account the sag in the process of generation of the images. This is of special importance when data from one modality is used to interpret or to correct data of another image from a different modality.

An aspect of some embodiments of the present invention relates to the use of a sag indicator, comprising a quantity of radiation absorbing material, which is large enough and dense enough to create a clear and measurable image in an imaging device, which is placed upon the stretcher, and which creates a clear and unique fiduciary location for the alignment process.

There is thus provided in accordance with some embodiments of the present invention a method for the correction of the effects of variable sag of a supporting element of a support system on an image of a subject, comprising acquiring an image of a subject at an imaging position and determining the sag of the supporting element at said imaging position. While in some embodiments the knowledge of the sag may be sufficient, in some embodiments it may be beneficial to adjust the image to compensate for the determined sag. Optionally the acquired image itself may be used to determine the sag, for example where a sag indicator placed on the surface of the supporting element is visible in the acquired image, or where a part of the supporting element is visible in the acquired image.

There is further provided in accordance with some embodiments of the present invention a method for the correction of the effects of variable sag of a supporting element on an image, comprising acquiring an image of a subject at a given imaging position, determining the sag of the support system at a longitudinal position of the supporting element different from the imaging position, using the determined sag to calculate the sag at the imaging position, and adjusting the image to compensate for the calculated sag.

Various methods of calculation may be used, for example by using an equation which relates the sag at one location on an extended supporting element to the sag at another location on an extended supporting element.

Optionally, the imaging which is used to determine the sag is CT imaging.

To align two different images of the same slice, there is further provided a method as above and additionally comprising acquiring a second image at a second imaging position, and aligning the images acquired at the two imaging positions, based on a differential sag for the two images.

In some embodiments the sag at one of the imaging positions is assumed to be zero.

In some embodiments the data accumulated from a plurality of various measurements of sag in a plurality of various situations is used to estimate the sag of a section of a subject in a particular situation.

There is further provided a method for the correction of the effects of variable sag of a supporting element of a support system on an image of a subject, comprising measuring the sag of the supporting element at a plurality of positions and under a plurality of controlled loads (for example a plurality of human-resembling dolls), retaining these sag measurements; estimating the sag at new positions and under the load of a subject using said data; and adjusting images taken of said subject to compensate for the determined sag. Optionally the estimation of the sag comprises interpolating or extrapolating from the accumulated data using a formula above, or the derivatives of these equations, for example a finite-difference relationship.

Optionally the methods may be used for various multi-modality imaging systems, in particular—CT and NM (for example PET or SPECT) imaging systems.

BRIEF DESCRIPTION OF THE DRAWINGS

Non-limiting embodiments of the present invention will now be described in the following detailed description, with reference to the attached drawings, in which like reference numbers indicate similar elements, and in which:

FIG. 3A is a schematic side drawing of a stretcher extended further from the table into another imaging volume (stretcher sag is exaggerated);

FIG. 3B is a schematic drawing of the far end of an extended stretcher in relationship to an imaging plane in an imaging volume;

These figures are designed for clarity of presentation, thus dimensions are not to scale.

DETAILED DESCRIPTION OF SOME EXEMPLARY EMBODIMENTS

Figure 1:
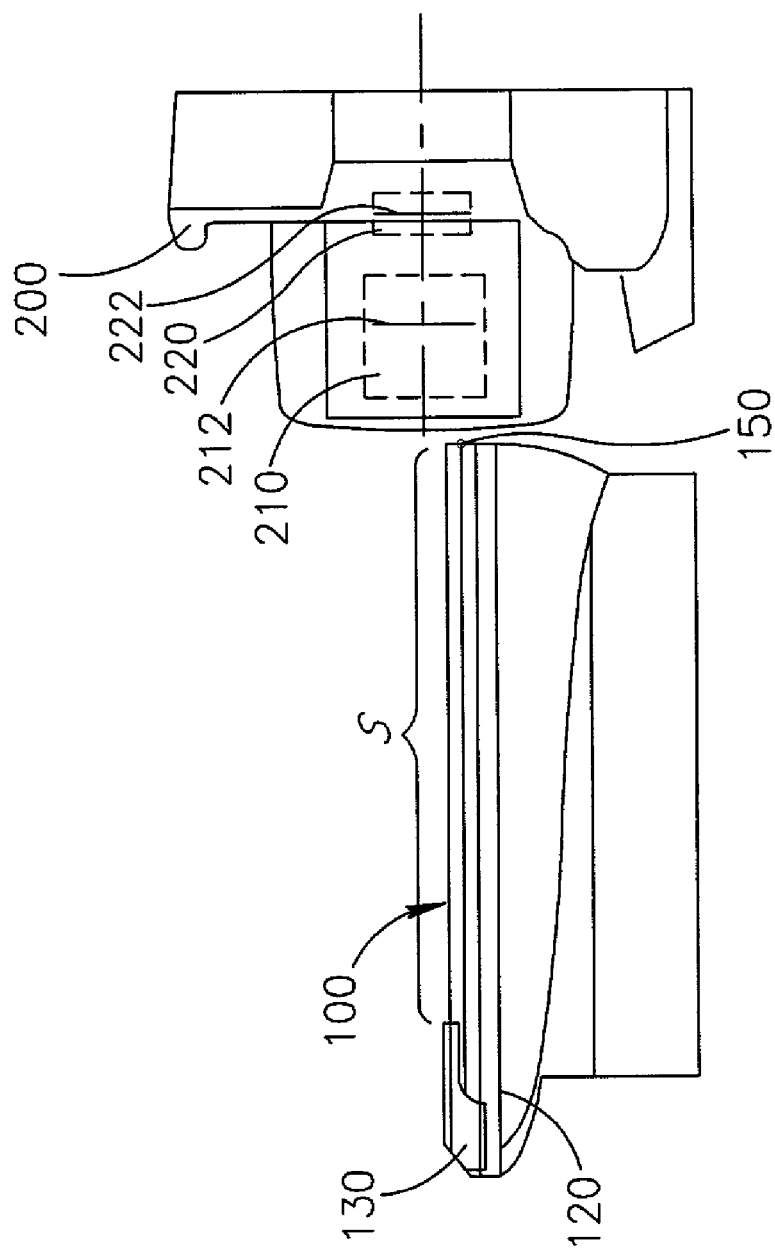
FIG. 1 is a schematic side drawing of a stretcher, supported by a table, in its initial position, before being extended from the table into an imaging gantry, in accordance with an exemplary embodiment of the invention.

FIG. 1 is a schematic drawing of a stretcher 100, supported by a table 120 in accordance with an exemplary embodiment of the present invention. Stretcher 100, of length S, is shown in its initial position, before being extended from the table into a gantry 200. A rear stretcher mount 130 holds the rear edge of stretcher 100 firmly. A front table roller 150 is located at or near to a front edge of table 120. When stretcher 100 is extended towards (and into) gantry 200, stretcher 100 is supported by front table roller 150 and held by rear stretcher mount 130.

Gantry 200 is shown having two imaging volumes: an far imaging volume 210 and an near imaging volume 220. Herein we describe an embodiment with one imaging plane in each imaging volume: a far imaging plane 212 in imaging volume 210 and a near imaging plane 222 in imaging volume 220. In some embodiments of the present invention there may be more than one imaging plane in one or more of the imaging volumes. Examples of systems in which two imaging volumes are present are described in patent application PCT/IL99/00300, filed 6 Jun. 1999, the disclosure of which is incorporated by reference. In the present patent application, a nuclear image, generated by any Nuclear Medicine technique, for example using Positron Emission Tomography or Single-Photon Emission Tomography (herein referred to as NM) is acquired in near imaging volume 210, and an X-ray CT image, which can be used for correcting the nuclear image, is acquired in far imaging volume 220.

In some embodiments imaging volumes 210 and 220 may be situated in separate gantries. Additionally or alternatively some of the imaging instrumentation may be located on the floor, at one or more sides of stretcher 100, and not supported by a gantry. In some embodiments of the present invention, instead of stretcher 100 there may be an alternative support mechanism to support the subject. Formulas in the following text which relate to a stretcher are appropriately changed when such support is used.

Figure 2:
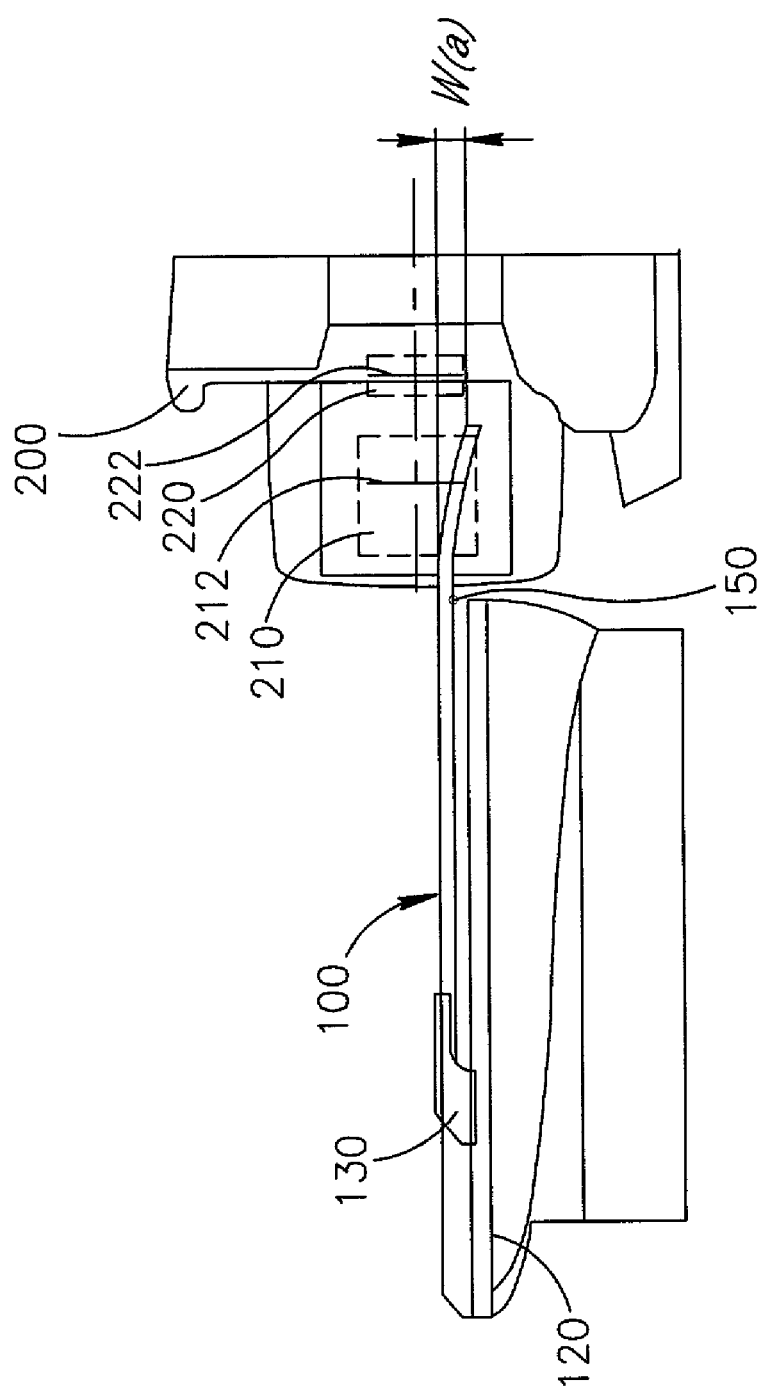
FIG. 2 is a schematic drawing of a stretcher partially extended from the table into the gantry (stretcher sag is exaggerated), in accordance with an exemplary embodiment of the invention.

FIG. 2 is a schematic drawing of a stretcher extended from the table into imaging volume 210 in the gantry. (Stretcher sag W(a) at the edge of stretcher 100 is exaggerated in the drawing for purposes of clarity.) In this imaging volume the sag of stretcher 100 is relatively small and directly measuring it may be problematical, especially if imaging of gamma rays is performed. The analysis below enables the calculation of the sag of those parts of stretcher 100 which are currently in volume 210, based upon measurements of sag W(Z) of the part of stretcher 100 which are currently in volume 220, as shown in FIGS. 3A and 3B, and described with respect to FIG. 4 and FIG. 5.

FIG. 3A shows stretcher 100 of total length S, measured from rear stretcher mount 130. Stretcher 100 extends from the table into far (CT) imaging volume 220 in gantry 200. (Stretcher sag W(a) at the edge of stretcher 100 is exaggerated in the drawing for purposes of clarity.) L is the length of that part of stretcher 100 which is supported by table 120 between rear stretcher mount 130 and front table roller 150. The stretcher extension $a(=S-L)$ is the length of that part of stretcher 100 which extends out from front table roller 150 in the direction of gantry 200. Since, in the present embodiment, imaging is done in imaging plane 212 and in imaging plane 222, it is necessary that the section (herein: "slice") of the part of the patient to be imaged is situated in the relevant imaging planes. The slice lies at a distance Z from rear stretcher mount 130, and must be brought to the relevant imaging plane. This is done by extending stretcher 100 by extension $a_1(Z)$ (or, if outer imaging plane is used for NM scanning—$a_{NM}(Z)$) for plane 212, and extension $a_2(Z)$ (or, if inner imaging plane is used for CT scanning—$a_{CT}(Z)$) for plane 222. Clearly, for different extensions there are different sags; thus when a particular slice which lies at a distance Z from rear stretcher mount 130 is located at plane 212, the sag is different from the sag when the same slice is located at plane 222.

In the present exemplary embodiment, when stretcher extension a is large enough that the edge of stretcher 100 reaches imaging plane 222, the sag of stretcher 100 at imaging plane 212 may be determined by measuring the sag in the far imaging system at plane 222 and calculating the sag in the near imaging system at plane 212. The sag at imaging plane 212 may thus be determined again at another extension of stretcher 100 further into volume 220, or even beyond volume 220.

As shown in FIG. 3A, when stretcher 100 is fully extended ($a=a_{max}$), the edge of stretcher 100 may extend into gantry 200 beyond imaging volume 220. In this situation a slice of the subject which is not at the end of stretcher 100, but at distance Z from rear stretcher mount 130, is located at imaging plane 222 in imaging volume 220. FIG. 3B shows sag W(a) at the edge of stretcher 100, and sag W(Z) at plane 222; the sags Ware exaggerated for clarity.)

Figure 4:
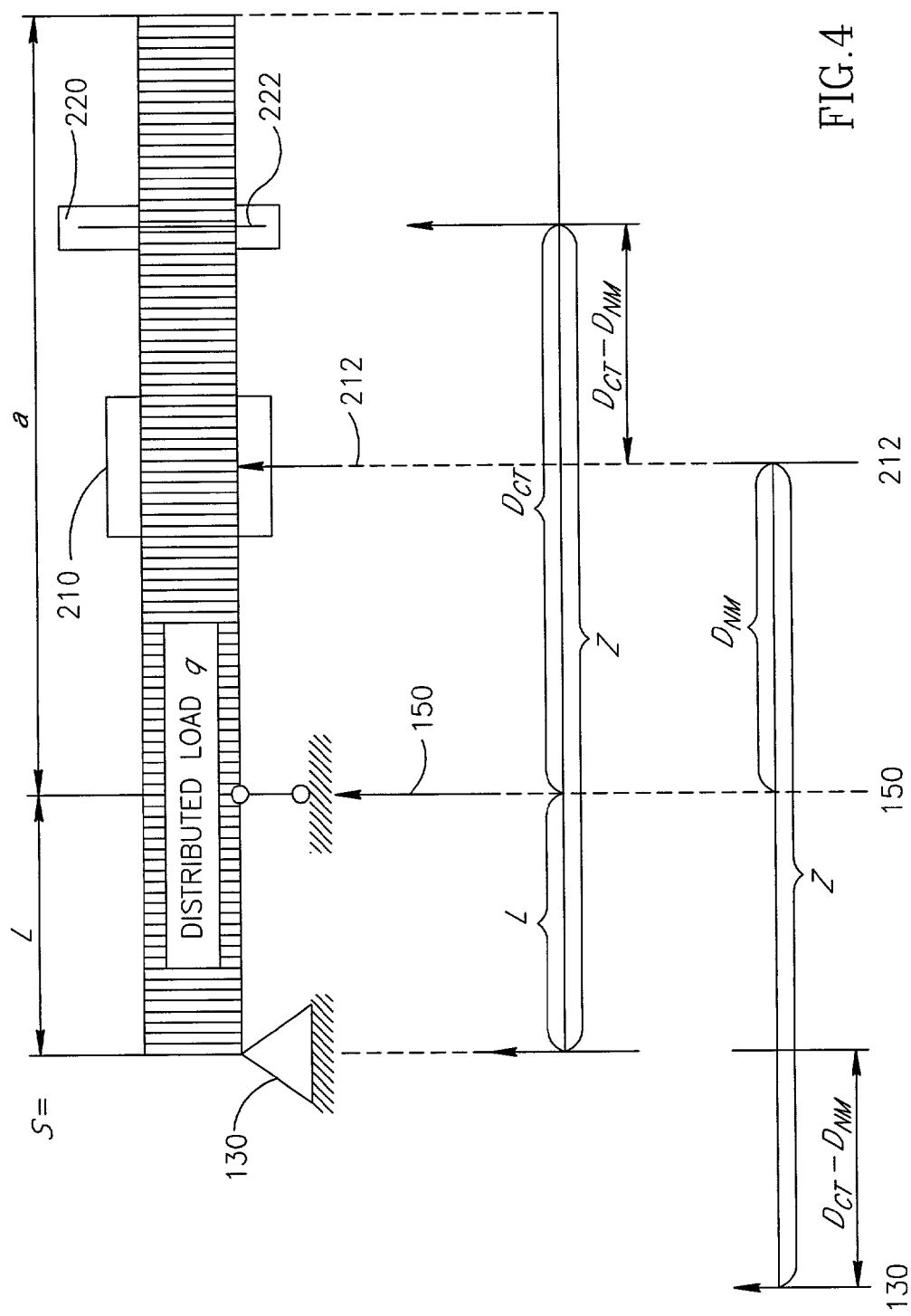
FIG. 4 is a schematic diagram of a loaded stretcher held at one end thereof and supported at an intermediate position thereof in accordance with an exemplary embodiment of the invention.

In FIG. 4, Z is the horizontal distance from rear stretcher mount 130 to the position of a slice of the subject of which the image is to be generated. In a multi-modality imaging system more than one image is taken of each slice. A CT image of each slice, located at distance Z from rear stretcher mount 130, is formed at imaging plane 222. $Z=L_{CT}+D_{CT}$ where $D_{CT}$ is the distance of imaging plane 222 from front table roller 150. Thus in order to take the CT image of the slice at location Z along stretcher 100, the extension $a_{CT}$ of stretcher 100 must be such that $L_{CT}=Z-D_{CT}$, or $S-a_{CT}=Z-D_{CT}$ or $a_{CT}=D_{CT}+S-Z$. In this formula S−Z represents the distance of the slice from the front edge of stretcher 100, and $D_{CT}$ is the distance of imaging plane 222 from front table roller 150. In other words: stretcher 100 must be extended so that its leading edge is brought to the location of the imaging plane, and further extended so that the slice will be brought to the imaging plane. Similarly to take the NM image of the slice at the imaging plane of imaging volume 210, the position of stretcher 100 must be $a_{NM}=D_{NM}+S-Z$ where $D_{NM}$ is the distance of the imaging plane 212 from front table roller 150. Hence $D_{CT}-D_{NM}$ is the distance between imaging planes 222 and 212, as indicated also by the definitions of $D_{CT}$ and $D_{NM}$.

For an extension a of stretcher 100 beyond front table roller 150, at any distance Z [$L<Z\leq L+a$; $L+a=S$] from the edge of rear stretcher mount 130 along the unsupported part of stretcher 100 between front table roller 150 and the free edge of stretcher 100, the sag W(Z) is:

$$W(Z) = -\frac{qL^4}{24EJ}\left[\left(4\frac{a^3}{L^3} - \frac{a}{L} + 3\frac{a^4}{L^4}\right) - \left(4\frac{a^2}{L^2} - 1 + 4\frac{a^3}{L^3}\right)\left(1 + \frac{a}{L} - \frac{Z}{L}\right) + \left(1 + \frac{a}{L} - \frac{Z}{L}\right)^4\right]$$ [Eq. 1]

where EJ is a deformation constant dependent on the material and geometric properties of the structure of stretcher 100.

The use of Eq. 1 in the present context is based upon the following assumptions:

(1) Imaging planes 212 and 222 are constant in position, at distance $D_{NM}$ and $D_{CT}$ from front table roller 150 respectively;

(2) the horizontal position of stretcher 100 is known: a, L and Z are variable and are measurable at any instant during the imaging process;

(3) Stretcher 100 is assumed to be of uniform EJ from rear stretcher mount 130 outward.

(4) The load distribution of the stretcher with the patient is effectively approximated by an equally distributed weight, although numerical methods may be used for unequal distributions;

(5) In some imaging areas, at some imaging planes, the vertical position of stretcher 100 is measurable.

Before Eq. 1 can be used, it is necessary to determine the "Load—Material coefficient"

$$\left(K = \frac{q}{24EJ}\right).$$

This may be done by measuring the sag W(a(Z)) at a point Z along stretcher 100 where a and L and Z are known, for example when the edge of stretcher 100 is at imaging plane 222 ($a=D_{CT}$; $L=S-D_{CT}$; $Z=S$).

Inverting Eq. 1 we get, in general, $$K = \frac{q}{24EJ} = \frac{-W}{L^4\left[\left(4\frac{a^3}{L^3} - \frac{a}{L} + 3\frac{a^4}{L^4}\right) - \left(4\frac{a^2}{L^2} - 1 + 4\frac{a^3}{L^3}\right)\left(1 + \frac{a}{L} - \frac{Z}{L}\right) + \left(1 + \frac{a}{L} - \frac{Z}{L}\right)^4\right]}$$ [Eq. 2]

Substituting the measured value of W, and the known geometric values of $a=D_{CT}$, $L=S-D_{CT}$, and $Z=S$ gives K.

Herebelow we present some exemplary methods of compensation for sag.

Figure 5:
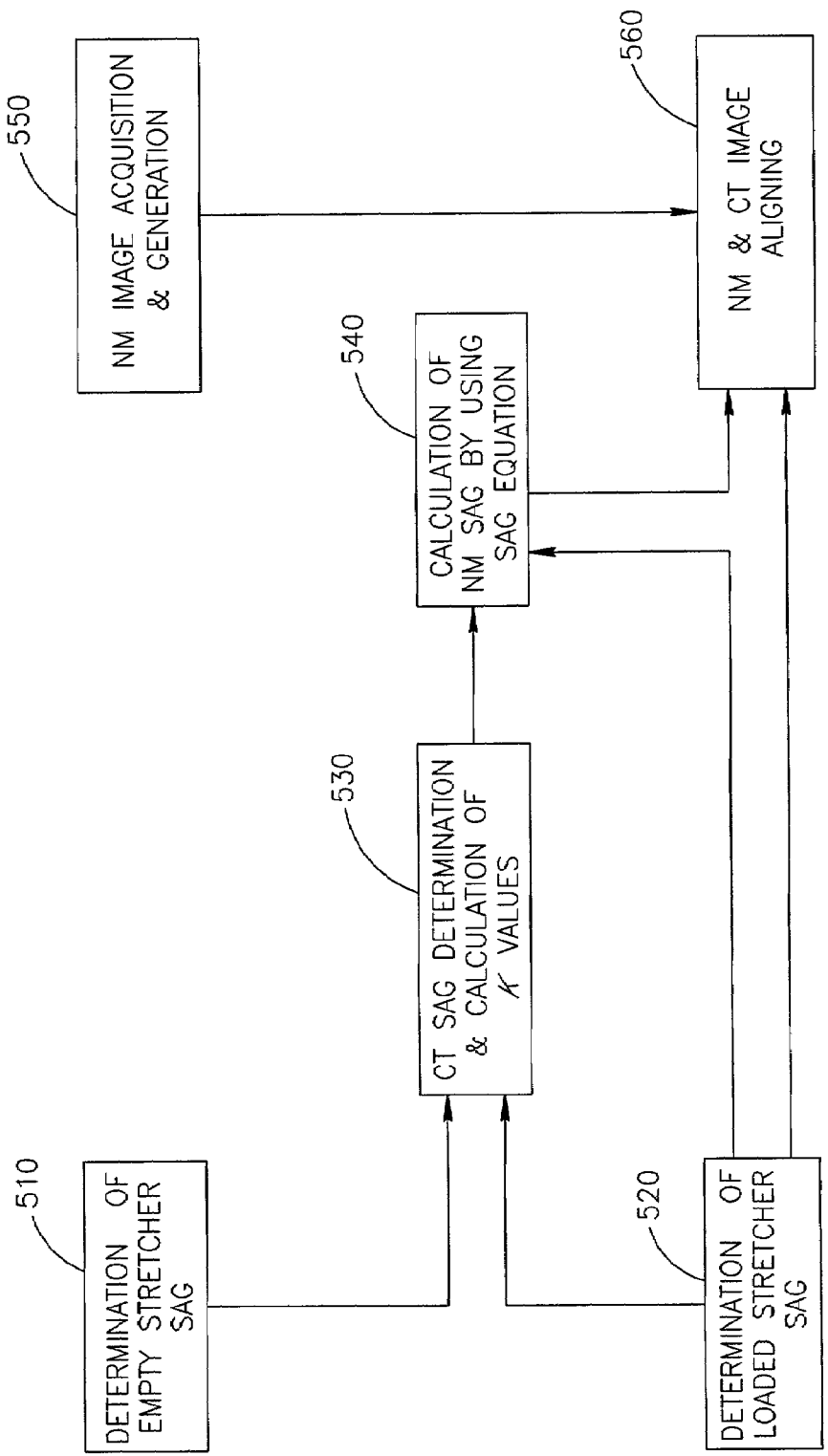
FIG. 5 is a block diagram of the acts taken in determining stretcher sag in accordance with an exemplary embodiment of the invention.

An exemplary direct method of compensating for the differential sag is schematically described in FIG. 5. In the first act (510) shown in FIG. 5, which need not be the first chronologically, the sag $W_0(a_{CT},Z)$ of empty stretcher 100 is determined for one or more extensions a of stretcher 100 and when corresponding points at Z along stretcher 100 are located at CT imaging plane 222. [Thus a measurement of EJ, independent of any patient, may be obtained, where the load distribution is that of stretcher 100 unloaded, which is close to an equal longitudinal weight distribution.] This determination of sag sag $W_0(a_{CT},Z)$ may be done only once the machine has been installed, although in practice it may be done for every patient or every day or after each adjustment of the multi-modality imaging system machine or of the support system. In act 520 the sag $W_L(a_{CT},Z)$ of loaded stretcher 100 is measured at CT imaging plane 222 for one or more sets of values a, L and Z, (not necessarily at the same values of a as in act 510). In this embodiment q is not measured directly, therefore the value of K=q/24EJ is unknown for each patient. Thus act 520 is performed for each patient.

In act 530 the differential sag of loaded stretcher 100 at extension a at imaging plane 222, $W(a_{CT},Z)=W_L(a_{CT},Z)-W_0(a_{CT},Z)$ is calculated for each pair of values of $a_{CT}$. Using Eq. 2 we derive values of K for each set of a and Z (L is uniquely determined by L=S−a) to use in Eq. 1, in act 540 below.

At act 540, the sag of stretcher 100 in imaging plane 212 $W(a_{NM},Z)$ is calculated for each value of Z, and for each value of $a_{NM}$, using Eq. 1 (above) with the value of K=q/24EJ (as determined at 530), with $a_{NM}=a_{CT}-(D_{CT}-D_{NM})$.

Act 550, which often precedes act 520, comprises the acquisition and generation of an image of a slice at Z in imaging plane 212 at $a_{NM}$.

The alignment of the image at Z generated at plane 212 (extension $a_{NM}$) is aligned (act 560) with the image of the slice generated at imaging plane 222 (extension $a_{CT}$) by adding the relative sag $\delta=w(a_{CT},Z)-W(a_{NM},Z)$ to the vertical location of the picture at imaging plane 222.

Alternatively both images may be aligned by adjusting each image to an arbitrary level, for example the W=0 level.

In the above method errors are generated due to the following problems:

a) discrepancies between the model of the cantilevered beam and the supporting element;

b) between the assumption of uniform distribution and a distribution resembling a real-life situation;

c) In the calculation in act 530 we use the formula $W(a_{CT},Z)=W_L(a_{CT},Z)-W_0(a_{CT},Z)$. For this to be accurate $a_{CT}$ and Z must be identical throughout—but $W_0(a_{CT},Z)$ is measured when stretcher 100 is empty, and we know the values of Z and of $a_{CT}$ which we use in $W_L(a_{CT},Z)$ only after the patient is positioned on stretcher 100! Nevertheless in some situations the inaccuracy is within allowed tolerances.

In an exemplary descriptive method, K and EJ are derived as functions of a and Z. Sag W(a,Z) is measured for each patient at additional extensions a and at additional positions Z along stretcher 100. A preferred position to measure W(a,Z) is at plane 222, at the maximal extension of stretcher 100: $a=a_{max}=D_{CT}+e$ where e is the maximum amount that stretcher 100 can be extended beyond plane 222. This position is the position of maximum sag for any given load. At this position Z=S−e and $L=S-a=S-(D_{CT}+e)=S-e-D_{CT}$. Having measured W(a,Z) at various pairs (a,Z), a series of measurements of EJ is obtained as a function of a and of Z. For any combination of a and Z, EJ is either known, having been measured, or can be interpolated. Knowing q=Q/S for the particular patient, −K is calculated. Using Eq.1 for every pair of values a,Z the sag W is derived (using L=S−a).

This method overcomes most of the inaccuracies due to discrepancies between the model of the cantilevered beam and the supporting element, but still assumes an even weight distribution along stretcher 100.

To further overcome inaccuracies due to the discrepancies due to the assumption of equally distributed weight, sag W is measured for various values of a and Z, using one or more weight distributions Q(Z) on stretcher 100 which resemble the weight distribution of a subject lying on stretcher 100. Human-resembling dolls with weight distributions close to reality are commonly used in the investigation of the response on the human body to situations of extreme stress, for example in automobile crashes. Thus a three dimensional array of sag values is prepared, with values for a, Z and Q. Using the values of W as a function of distances a, Z and of the weight distributions Q, it is possible to either choose W(a,Z,Q) from the table of measured values, or to interpolate for values not measured. Various well known methods of interpolation may be used, although a preferable method uses the derivatives of Eq. 1 for interpolation.

In some embodiments where the sag of stretcher 100 in imaging plane 210 is negligible it is possible to set $W_{NM}=0$, and to compensate only for $W_{CT}$.

Figure 6:
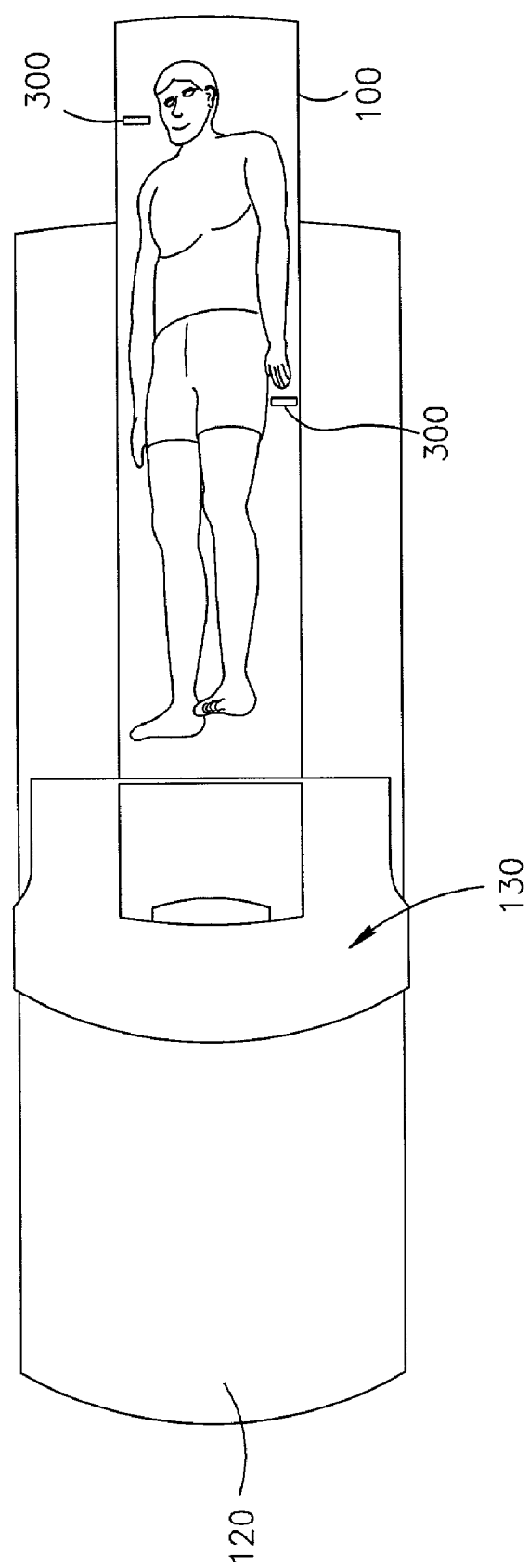
FIG. 6 is a schematic drawing of a stretcher with sag indicators in accordance with exemplary embodiments of the invention.

FIG. 6 is a schematic drawing of stretcher 100 with a sag indicator 300, in accordance with an exemplary embodiment of the present invention. Sag indicator 300 is an aid to measurement of the position of stretcher 100, to determine correction for the sag. A sag indicator 300 is shown placed, or affixed, near the head area. This position of sag indicator 300 is appropriate for a case where the slices to be imaged lie in the head. In some embodiments, sag indicator 300 is a straight piece of material with a moderate absorption coefficient for the image-creating signals (e.g. radiation, in imaging systems based upon radiation) used in at least one of the imaging systems. In the present exemplary embodiment, imaging volume 220 is used for X-ray computed tomography, and sag indicator 300 has a moderate X-ray absorption coefficient. For some imaging systems, for example where imaging volume 210 is used for gamma ray imaging, the radiation is detected from many angles in the imaging plane. In some embodiments the detectors surround the subject, and sag indicator 300 has a relatively low absorption coefficient for the radiation used in these systems. In some situations more than one sag indicator may be used, for example when the sag must be very accurately known in different sections of the patient. Thus in FIG. 6 two sag indicators 300 are shown: one near the head and one near the bottom of the spine. Alternatively a single axially extended sag indicator may be placed on or alongside stretcher 100, which will enable measuring the sag at various places along its length.

In some embodiments, the material of which some (preferably linear) part or parts of stretcher 100 is made has a moderate absorption coefficient for the waves used in one of the imaging modalities, and may be used to determine the sag in the imaging volume of that modality.

In some embodiments the array of sag values W is measured when stretcher 100 is manufactured, using the imaging machine itself, as follows: a plurality of sag indicators and plurality of NM radiation sources are affixed to stretcher 100. The sag is measured at plane 222 in the CT area using a sag indicator as described above, and simultaneously using a substantially planar or point source of NM radiation located on stretcher 100—the sag at plane 212 in the NM area is directly measured, thus establishing empirical correlations between sags. Preferentially, such measurements are made using human-resembling dolls as mentioned above, so that the weight distribution is close to reality. Additionally or alternatively, mechanical and/or wave based distance measuring devices, for example optical devices, may be used to determine sag, in either the CT area, the NM area, or both. Thus a realistic three dimensional array of sag values is prepared, with values for a, Z and Q. Using the values of W as a function of distances a, Z and of the weight distributions Q, it is possible to either choose W(a,Z,Q) from the table of empirical values, or to calculate values not empirically measured. Various well known methods of interpolation and extrapolation may be used, although a preferable method uses the derivatives of Eq. 1.

In some other embodiments, or in another mode of operation of a multi-modality imaging system, stretcher 100 is continuously extended (a changes continuously) as the subject is continuously transported through the imaging volumes, while the imaging systems operate. In such cases, it is not necessary to continuously measure the sag, since the sag value is a continuously changing variable. It is sufficient to measure the sag at intervals. In some embodiments the intervals may be fixed in position. In some embodiments the intervals may be determined otherwise, for example individually, at positions considered critical to the patient.

Some embodiments of the present invention relate not to human subjects or patients but to other subjects which are being investigated by imaging. In some embodiments instead of a stretcher 100 there may be other support systems to support the subject of the multi-modality imaging process.

The present invention has been described using non-limiting detailed descriptions of some embodiments thereof that are provided by way of example and are not intended to limit the scope of the invention. Details shown with respect to one embodiment of the invention, may be used with other embodiments, if suitable for such embodiments. Further, some details of some embodiments are non-essential. Furthermore, while some features of the embodiments are described in terms of particular examples thereof, it should be understood that these features are mere examples of broader classes of features which may be employed. Similarly, some features may be omitted in some embodiments of the invention. Variations of embodiments described will occur to persons of the art. Furthermore, the terms "comprising," "comprise," "include," and "including" or the like, shall mean, when used in the claims, "including but not necessarily limited to."

The invention claimed is:

1. A method for the determination of variable sag of a supporting element of a support system supporting a subject comprising:
   (a) acquiring an image of a slice of the subject at an imaging position; and
   (b) determining said sag of said support element at said imaging position utilizing a quantity of radiation absorbing material, which is large enough and dense enough to create a clear and measurable image in an imaging device.

2. A method according to claim 1, further comprising adjusting said image to compensate for said determined sag.

3. A method as in claim 2 in which said acquired image is used for determining said sag.

4. A method as in claim 2 in which said acquired image is a CT image.

5. A method as in claim 2 in which said acquired image is an NM image.

6. A method as in claim 1 in which said quantity of radiation absorbing material is comprised in said supporting element.

7. A method for the determination of variable sag of a supporting element of a support system supporting a subject at an imaging position at which an image of a slice is acquired, comprising:
   (a) determining the sag of said supporting element at at least one longitudinal position of said supporting element, different from the imaging position of said supporting element at which said image of a slice is acquired, utilizing at least one quantity of radiation absorbing material, which is large enough and dense enough to create a clear and measurable image in an imaging device, and which is located at at least one longitudinal position different from said imaging position, for determining said sag at said imaging position; and
   (b) using said sag determined at said at least one longitudinal position of said supporting element different from said imaging position to determine said sag at said imaging position.

8. A method as in claim 7, further comprising adjusting of said image to compensate for said determined sag.

9. A method as in claim 7 in which said image is an NM image.

10. A method for the correction of the effects of different sags of a supporting element on more than one image of one slice of a subject, comprising:
    (a) acquiring at least one image of said slice at an imaging position using a first imaging modality;
    (b) acquiring another image of said slice at a different imaging position using a second imaging modality;
    (c) determining the sag at at least one of said imaging positions from an image acquired at the other imaging position; and
    (d) aligning said acquired images based on the determined sag.

11. A method as in claim 10 in which at least one of said images is an NM image.

12. A method as in claim 12 in which at least one of said images is a CT image.

13. A method according to claim 12 wherein determining the sag is performed on said CT image.

14. A method as in claim 10 comprising determining the sags of said supporting element at both of said imaging positions, and aligning said acquired images.

15. A method according to claim 14 in which said aligning of said acquired images is performed by aligning said images to an arbitrary level.

16. A method according to claim 10 wherein said sag at one of the imaging positions is assumed to be zero.

17. A method according to claim 10 wherein the determination of said sag of said slice at one imaging position is performed by calculation based on said sag of said supporting element determined at another imaging position.

18. A method according to claim 10 comprising the adjustment of said images to compensate for the difference between said sags at said two imaging positions.

19. A method according to claim 17 comprising the adjustment of said images to compensate for the difference between said sags at said two imaging positions.

20. A method according to claim 10 wherein at least one of said images is a CT image.

21. A method according to claim 10 wherein at least one of said images is an NM image.

22. A method according to claim 10 wherein said image of said slice, of which said sag is determined, is a CT image, and said other image is an NM image.

23. A method according to claim 22 in which at least one quantity of radiation absorbing material, which is large enough and dense enough to create a clear and measurable image in an imaging device, is used for determining said sag of said supporting element at said position at which sag is measured.

24. A method for the correction of the effects of different sags of a supporting element on more than one image of one slice of a subject, comprising:
    (a) acquiring at least one image of said slice at an imaging position;
    (b) acquiring another image of said slice at a different imaging position;
    (c) determining the sag at at least one of said imaging positions;
    (d) aligning said acquired images based on the determined sag; and
    (e) calculating said sag based upon the following model: a support element of length S is extended beyond its base by an extension a, the remainder of said support element, which is the supported part of the support element, is of length L; the distance of said imaged slice from supported edge of the support element is Z; said support element is assumed to be of uniform deformation constant EJ dependent on the material and geometry of the supporting element; the load distribution of the support element with the subject is effectively approximated by an linearly equally distributed weight q along the length of said support element; and using the equation $$K = \frac{q}{24EJ} = \frac{-W}{L^4\left[\left(4\frac{a^3}{L^3} - \frac{a}{L} + 3\frac{a^4}{L^4}\right) - \left(4\frac{a^2}{L^2} - 1 + 4\frac{a^3}{L^3}\right)\left(1 + \frac{a}{L} - \frac{Z}{L}\right) + \left(1 + \frac{a}{L} - \frac{Z}{L}\right)^4\right]} \quad \text{[Eq. 2]}$$

25. A method for the correction of the effects of different sags of a supporting element on more than one image of one slice of a subject, comprising
    (a) the accumulation of data from a plurality of various measurements of sag in a plurality of various situations, and (b) the utilization of said accumulated data to estimate the sag of a slice of a subject in a particular situation.

26. A method for the correction of the effects of variable sag of a supporting element of a support system on an image of a subject, comprising:
   (a) measuring the sag of the support element at a plurality of positions and under a plurality of controlled loads;
   (b) storing these sag measurements;
   (c) estimating the sag at an imaging position and under the load of a subject using said stored sag measurements; and
   (d) adjusting an image taken of said subject at said imaging position to compensate for the estimated sag.

27. A method of estimating the sag of a supporting element of a support system of a patient at a first position based on a determination of the sag of the supporting element at a second imaging position of the supporting element that is not adjacent to the first position, the method comprising:
   determining the sag of the support system at the second imaging position; and
   estimating the sag of the support system at the first imaging position, based on the sag determined at the second imaging position.

28. A method according to claim 27 wherein the determination of the sag is based on an image taken at the second imaging position.

29. A method according to claim 28 wherein the second imaging position is a position at which a computerized tomography image is acquired.

30. A method according to claim 29 wherein the first imaging position is a position at which a nuclear image is acquired.

31. A method according to claim 28 wherein the first imaging position is a position at which a nuclear image is acquired.

32. A method according to claim 27 wherein the supporting element is attached to a support at a first position thereof, as a cantilever support.

33. A method according to claim 27 wherein the first imaging position is nearer to said support then is the second imaging position.

34. Imaging apparatus comprising:
   a first, nuclear or MRI, imager which produces an image of a patient at a first imaging position along an axis; and
   a second, CT, imager which produces a CT image of a patient at a second imaging position axially displaced from the second imaging position;
   a table operative to transport a patient substantially along said axis such that portions of the patient are imaged by said first and second imaging positions;
   said CT imager being configured and operative to determine sag of said table at said second position from said CT image; and to estimate the sag of the table at the first position from the sag determined at the second position.

* * * * *